[19] United States Patent
Lowth

[11] 3,953,895
[45] May 4, 1976

[54] HOSIERY FOR WEAR
[75] Inventor: Leonard Cecil Lowth, London, England
[73] Assignee: Scholl, Inc., Chicago, Ill.
[22] Filed: July 3, 1974
[21] Appl. No.: 485,745

[30] Foreign Application Priority Data
July 4, 1973 United Kingdom............... 31863/73

[52] U.S. Cl......................................... 2/240; 2/409
[51] Int. Cl.². ........................................... A41B 9/04
[58] Field of Search............ 2/224 R, 240, 227, 225, 2/226, 239; 66/177

[56] References Cited
UNITED STATES PATENTS
3,547,128  12/1970  Keltner ........................... 2/224 R X FOREIGN PATENTS OR APPLICATIONS
1,555,776  12/1968  France .................................. 2/224 R
1,925,302  5/1969  Germany.............................. 2/224 R Primary Examiner—H. Hampton Hunter
Attorney, Agent, or Firm—Hill, Gross, Simpson, Van Santen, Steadman, Chiara & Simpson

[57] ABSTRACT

An article of wearing apparel comprising a leg portion shaped substantially to cover at least the upper part of one of a wearer's legs, and a body portion extending upwardly from the leg portion at least to waist height and capable of substantially covering the lower part of the wearer's body, an aperture being provided in said article through which said wearer's other leg passes when said article is worn by said wearer.

4 Claims, 3 Drawing Figures

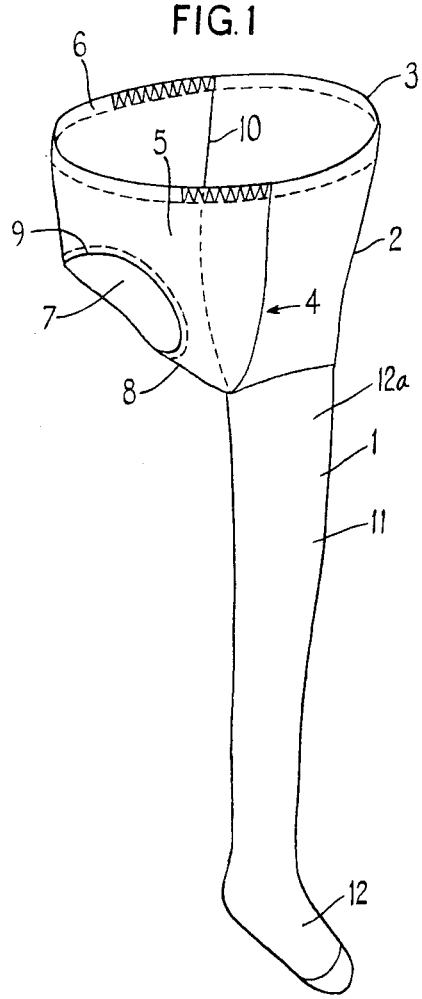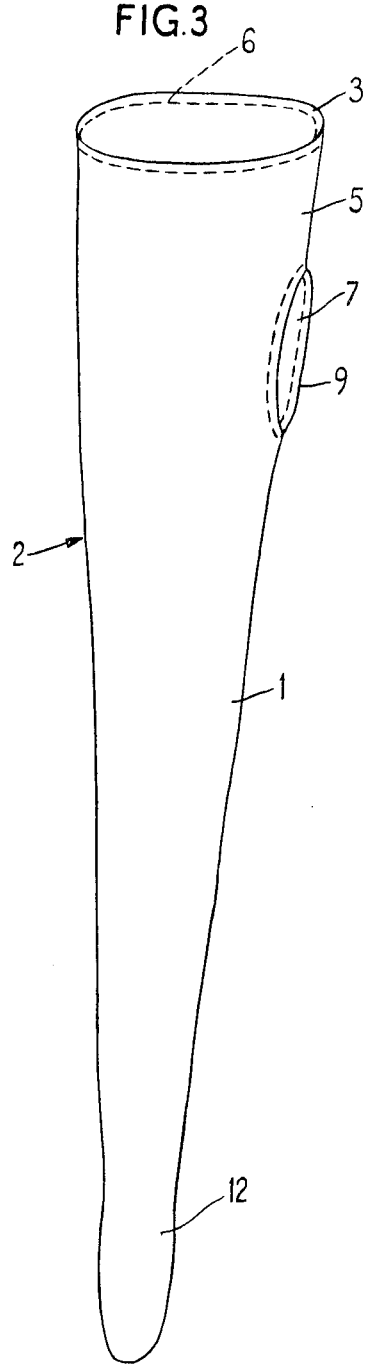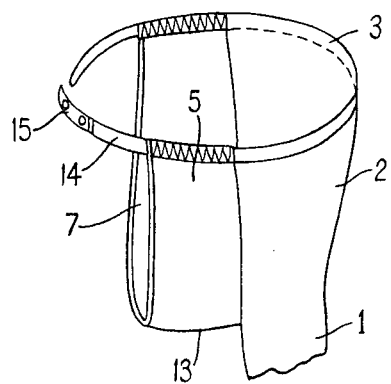

HOSIERY FOR WEAR

BACKGROUND OF THE INVENTION

1. Field of the Invention

This invention relates to hosiery for wear by men, women or children including surgical hose.

2. Description of Prior Art

A form of hosiery frequently used especially by girls and women, known as tights, comprises two leg portions in the form of ladies stockings, the upper ends of which are carried up into a single body portion covering the crotch and having a part encircling the wearer's body and termination at its top portion in a waistband which grips the wearer's waistline and prevents the garment slipping down.

One disadvantage of such tights is that if one leg portion is damaged as by laddering in a knitted material or is torn, the garment becomes useless at least for smart wear. Also to put the tights on, especially when made of elastic material, as for surgical use to give support to the lower parts of the wearer's body, the wearer has to put each leg portion on in turn; many wearers of elastic tights are suffering from some disability such as varicose veins and frequently are of advancing years so that they have difficulty, particularly in drawing the second leg portion on to their leg and also in drawing the body portion up over their thighs and over their body. This is particularly emphasised when the body portion is elastic to support the abdomen of a wearer suffering from abdominal varicose veins for example.

The main object of the present invention is to provide an article of hosiery for male or female use in which these disadvantages are reduced.

SUMMARY

According to the present invention an article of wearing apparel comprises a leg portion shaped substantially to cover at least the upper part of one of a wearer's legs and a body portion extending upwardly from the leg portion at least to waist height and capable of substantially covering the lower part of the wearer's body, an aperture being provided in the article through which the wearer's other leg passes when the article is worn by the wearer.

Preferably the leg portion extends from the upper part of the wearer's thigh to below the wearer's knee.

The body portion may be stretchable to form a pant like portion round the lower part of the wearer's body from the waistline downwards.

In use the wearer draws the leg portion over one leg, passes the other leg through the aperture and pulls the body portion up over the lower part of the body until the waistline of the body part is comfortably round the waist of the wearer's body. The wearer may then don a similar article on the other leg passing the clothed first leg through the aperture and drawing the leg portion over the unclothed leg until the body portion is fully in place with its waistline round the wearer's waistline thus simulating a pair of tights with the lower part of the wearer's body clothed in a double thickness of material. The second leg may however be covered by a conventional stocking.

In a preferred construction, the leg portion is made of knitted hosiery material and the body portion is made of a preferably different fabric such as stretch nylon woven fabric or knitted fabric or of cotton or wool.

The waistline of the body portion is preferably provided with an elastic formation which may be stretchable to the dimensions of the wearer's waist. Such elastic means may be built into the garment or an elastic band attached to the garment or the garment may have a waistline double hem within which an elastic band is inserted, an opening being provided if desired for replacing expended elastic materials.

The aperture may be surrounded by an elastic portion formed in the same way as the waistline to grip round the thigh of the wearer's other leg. Alternatively, the body portion may be completely open on the outside of the wearer's leg so that the whole thigh is outside the garment in wear and the substantially vertical edge of the body portion may then be provided as for the waistline with an elastic construction for engaging against the wearer's body.

BRIEF DESCRIPTION OF THE DRAWINGS

FIG. 1 is a perspective view showing diagrammatically an article of wearing apparel;

FIG. 2 shows an alternative construction only the upper portion of the leg portion being shown; and, FIG. 3 shows an article of clothing of the invention.

In the drawings, the same references are used to designate the same or similar parts.

DESCRIPTION OF PREFERRED EMBODIMENTS

Referring to FIG. 1, the article of apparel preferably of hosiery comprises a leg portion 1 extending on the outside 2 up to the waistline 3 and on the crotch side 4 extends into a body portion 5 which completes the waistline at its upper portion 6, and has an aperture 7 in its lower portion 8, the margin 9 of which surrounds the wearer's thigh of the other leg.

In FIG. 1 the article is being shown as separate leg and body portions which are united together as by sewing along the line 10 but it is to be understood that the whole garment may be formed in one piece.

The leg portion is shown as made of elastic hose and includes a leg 11 and a foot 12 but it will be understood that it may be only a half leg down to just below the knee or only cover the thigh. The stocking part will itself be formed to suit the requirements of the wearer which, if it is in the form of surgical hose or elastic hose to support the whole or part of the wearer's body, such as a sufferer of varicose veins. The leg portion indicated at 12a may be elastically reinforced in order to give support to the wearer's leg above the knee and below the thigh but the elastic portion may extend up to the thigh or further down the leg or any other arrangement to suit the wearer's requirements.

The leg portion is preferably knitted in the manner of ladies stockings and for surgical use is provided with elastic thread or stretchable thread formation as is conventional in elastic or surgical stockings.

The body part 5 may be of any suitable material such as woven or knitted, brushed or stretch nylon or cotton or wool.

Referring to FIG. 2 this shows an alternative form of garment having the leg portion 1 with the upper outside portion 2 extending to the thigh in a waistline 3 as in FIG. 1. The body portion 5 however is formed as a substantial width crotch strip portion 13 along the inner side of the outside body portion 2, in the area of the crotch and which extends down from the waistline at the front of the article and thus at the front of the wearer and provides a crotch-covering loop between the legs and then extends up to the waistline at the back of the garment and thus of the wearer. Its aperture 7 is formed by a complete opening defined by the side of the crotch portion opposite from the upper outside leg portion 2. The hem at the opening defined by the crotch strip 13 may be formed with an elastic construction as for the aperture in FIG. 1 and the waist band 14 may exend right round the waistline as for FIG. 1 and may be broken as at 15 and the two parts may be connected together by buttons, hooks and eyes, Velco fastenings or other means to ensure the close fitting of the waistline round the waistline of the wearer.

It will be apparent that when the wearer dons similar, allochiral garments according to FIG. 2 on both legs, the crotch strips 13 will overlap relatively adjustably and provide a double thickness in the crotch area, but there will be only a single thickness in the upper outside portions 2 which may be a preferred relationship for coolness and ease of flexing at the hips.

Referring to FIG. 3 this shows a third construction in which the body portion is in one piece with the leg portion and may form a continuation of the leg portion and being extendable or stretchable to cover at least the main portion of the lower portion of the wearer's body.

In use the articles shown in the drawings are for the left legs of wearers but they could be so shaped that they fit either leg. To don the articles the wearer first passes one foot through the waistline and then draws the complete stocking onto leg and foot drawing the stocking up to its full height on the leg and then pulling the body portion up to the waist of the body. During this operation the other leg is passed through the aperture 7 in FIGS. 1 and 3, while in FIG. 2 the other leg remains free and the wearer's thigh remains exposed at that side of the body until a counterpart garment is donned. The second counterpart article formed for the right leg if used is then donned in the same way as the first portion so that the wearer then has, in effect, a simulated pair of tights with a double thickness of material round the lower part of the body (FIGS. 1 and 3), or with a double thickness of material in the crotch portion and centre and back of the lower part of the body (FIG. 2).

By means of such garments adequate support can be provided to suit the wearer's requirements, particularly in the case of elastic and surgical stockings and the cost of the article is reduced in that, if one leg portion is damaged, the other leg portion can still be used with a new second leg portion.

I claim:

1. An article of wearing apparel comprising a leg portion shaped substantially to cover at least the upper part of one of a wearer's legs and an upper outside body portion extending upwardly from the leg portion at least to waist height for engaging the wearer's thigh in line with said one leg, and comprising:

a substantial width crotch strip connected along the inner side of said outside body portion and extending down from the waistline at the front of the article and then providing a crotch-covering loop and extending up to the waistline at the back of the article;

said crotch strip defining a complete opening extending from the waistline to the crotch at its side which is opposite from said upper outside body portion;

whereby when the article is worn on one of the wearer's legs and associated hip, the remaining leg and the hip will remain free until a second counterpart garment is donned on said other leg and provides a thigh covering body portion for said other hip;

and a waistband extending entirely around the waistline to which said outside body portion and said crotch strip are attached.

2. An article according to claim 1 wherein said waistband is separable at the open side of said crotch strip and provides two parts which may be connected together, and means for connecting said parts together around the waistline of a wearer of the article.

3. An article according to claim 1, wherein said leg portion is in the form of a complete leg and foot covering stocking.

4. An article according to claim 1, comprising a waistband about said waistline, said waistband being elastic.

* * * * *